United States Patent
Patel

(10) Patent No.: US 10,835,481 B2
(45) Date of Patent: Nov. 17, 2020

(54) USE OF UV RESISTANT ACTIVE MATERIALS ON HAIR

(71) Applicant: COAST SOUTHWEST, INC., Placentia, CA (US)

(72) Inventor: Amit Patel, Placentia, CA (US)

(73) Assignee: COAST SOUTHWEST, INC., Placentia, CA (US)

( * ) Notice: Subject to any disclaimer, the term of this patent is extended or adjusted under 35 U.S.C. 154(b) by 195 days.

(21) Appl. No.: 15/923,357

(22) Filed: Mar. 16, 2018

(65) Prior Publication Data

US 2018/0263891 A1 Sep. 20, 2018

Related U.S. Application Data

(60) Provisional application No. 62/472,054, filed on Mar. 16, 2017.

(51) Int. Cl.
| | | |
|---|---|---|
| *A61K 8/898* | (2006.01) | |
| *A61K 8/86* | (2006.01) | |
| *A61Q 17/04* | (2006.01) | |
| *C08G 77/54* | (2006.01) | |
| *C08G 77/26* | (2006.01) | |
| *C08G 77/14* | (2006.01) | |
| *C08G 65/00* | (2006.01) | |
| *C08G 77/12* | (2006.01) | |

(52) U.S. Cl.
CPC .............. *A61K 8/898* (2013.01); *A61K 8/86* (2013.01); *A61Q 17/04* (2013.01); *C08G 65/00* (2013.01); *C08G 77/12* (2013.01); *C08G 77/14* (2013.01); *C08G 77/26* (2013.01); *C08G 77/54* (2013.01)

(58) Field of Classification Search
CPC .......... A61K 8/86; A61K 8/898; A61Q 17/04; C08G 65/00; C08G 77/12; C08G 77/14; C08G 77/26; C08G 77/54
See application file for complete search history.

(56) References Cited

U.S. PATENT DOCUMENTS

| | | |
|---|---|---|
| 2,798,053 A | 7/1957 | Brown |
| 3,755,560 A | 8/1973 | Dickert et al. |
| 4,421,769 A | 12/1983 | Dixon et al. |
| 4,509,949 A | 4/1985 | Huang et al. |
| 4,599,379 A | 7/1986 | Flesher et al. |
| 4,628,078 A | 12/1986 | Glover et al. |
| 4,835,206 A | 5/1989 | Farrar et al. |
| 4,849,484 A | 7/1989 | Heard |
| 5,011,681 A | 4/1991 | Ciotti et al. |
| 5,087,445 A | 2/1992 | Haffey et al. |
| 5,100,660 A | 3/1992 | Hawe et al. |
| 5,698,183 A | 12/1997 | Langer et al. |
| 8,362,185 B2 * | 1/2013 | Wagner .................. A61K 8/898 528/20 |
| 2003/0108494 A1 * | 6/2003 | Fender .................. A61K 8/898 424/59 |
| 2006/0188456 A1 | 8/2006 | Ferenz et al. |
| 2015/0093420 A1 * | 4/2015 | Snyder .................. A61K 8/042 424/401 |

FOREIGN PATENT DOCUMENTS

WO    WO 2004/043412    5/2004

OTHER PUBLICATIONS

Invitation to Pay Additional Fees issued in International Patent Application No. PCT/US2018/022945, dated Jun. 4, 2018.
International Search Report and Written Opinion issued in International Patent Application No. PCT/US2018/022945, dated Aug. 20, 2018.

* cited by examiner

*Primary Examiner* — Anna R Falkowitz
(74) *Attorney, Agent, or Firm* — Norton Rose Fulbright US LLP

(57) ABSTRACT

Polymers comprising at least one cationic functional group and at least one ultraviolet light-absorbing compound are disclosed herein. The resulting polymers exhibit ultraviolet light-absorbing properties and may be used in sunscreen compositions for skin and/or hair.

4 Claims, No Drawings

USE OF UV RESISTANT ACTIVE MATERIALS ON HAIR

CROSS REFERENCE TO RELATED APPLICATIONS

The present invention claims priority to U.S. Application 62/472,054 filed Mar. 16, 2017; the disclosure of which is incorporated herein by reference.

FIELD OF THE INVENTION

This invention relates to the field of personal care products that include sunscreens.

BACKGROUND

It is well known that over-exposure to sunlight can be harmful. The component of sunlight with wavelengths ranging from 100-400 nm is known as ultraviolet light or radiation, and can damage skin and hair fiber.

In the short term, over-exposure to ultraviolet radiation present in sunlight can cause the skin to darken and sunburn. In the long term, the sun's ultraviolet light damages elastin fibers in the skin, causing the skin to sag, stretch, and lose its ability to go back into place after stretching.

Ultraviolet light is also known to damage hair. Dryness, reduced strength, rough surface texture, loss of color, decreased luster, stiffness, and brittleness of hair are caused by exposure to the sun's ultraviolet light. Chemically, these changes are believed to be caused by UV light-induced oxidation of the sulfur-containing molecules within in the hair shaft. Colorants or dyes in color-treated hair are also susceptible to ultraviolet light-induced degradation.

Sunscreens have been available for over 80 years and today play a major role in skin cancer prevention and sun protection. Sunscreen compositions employ two types of materials to reduce the amount of harmful ultraviolet light that reaches the skin. Ultraviolet light-absorbing materials, such as p-amino benzoic acid, are organic compounds with conjugated $\pi$-electron systems that absorb ultraviolet light and convert the absorbed energy into heat. Ultraviolet light scattering materials, such as zinc oxide and titanium dioxide, are solid inorganic particles that physically block and scatter sunlight.

There is an increasing need for sunscreen compositions in a population that is exposed to an increasing amount of damaging sunlight. Although the benefits of sunscreens are well known, issues with currently available sunscreens exist. Sunscreen vehicles often determine product efficacy. To maintain the photoprotective properties and photostability of ultraviolet-absorbing and/or ultraviolet-blocking components, a sunscreen vehicle must minimize interaction of inert/active ingredients. To maintain proper mixtures, sunscreens must be formulated to avoid or impede de-emulsification and settling.

SUMMARY

The present disclosure provides a solution to the problems associated with current sunscreen compositions. The solution resides in providing that exhibit both ultraviolet protection and appealing satisfactory rheological properties. It is therefore an object of the present disclosure to provide novel sunscreen compositions that employ ultraviolet light-protective compounds that assist in maintaining suspensions and emulsions. In some embodiments, the ultraviolet light-absorbing compounds disclosed herein help or prevent sunscreen compositions from falling out of solution. In further embodiments, the ultraviolet light-absorbing compounds disclosed herein help maintain sunscreen composition emulsions or suspensions.

In some aspects, an ultraviolet light-absorbing polymer is disclosed. In some embodiments, the ultraviolet light-absorbing polymer comprises at least one cationic functional group and at least one ultraviolet light-absorbing component. Without wishing to be bound by theory, a polymer comprising an ultraviolet light-absorbing component may help the ultraviolet light-absorbing component stay in an oil phase or emulsion. In some embodiments, an ultraviolet light-absorbing component that remains in emulsion or suspension will improve sun protection factor (SPF) per unit sunscreen. In some aspects, improved SPF per unit sunscreen allows a sunscreen composition to employ or incorporate less ultraviolet light-absorbing compound.

In some embodiments, an ultraviolet light-absorbing polymer may comprise a plurality of cationic functional groups, which may be the same or different. In further embodiments, an ultraviolet light-absorbing polymer may comprise a plurality of ultraviolet light-absorbing components, which may be the same or different. In some embodiments, the cationic functional group is a quaternary amine or a tertiary sulfonium. The at least one ultraviolet light-absorbing component may be an ultraviolet light-absorbing compound that is covalently bound to the polymer. The at least one ultraviolet light-absorbing component or compound may directly bound to the polymer, or a tether or chemical linker may be used to link the ultraviolet light-absorbing compound to the polymer. In some embodiments, a polymer is endblocked with at least one quaternary amine. Quaternary amines adhere to hair fibers and may assist in retention of a polymer bound to an ultraviolet light-absorbing component.

In some embodiments, an ultraviolet light-absorbing polymer comprising at least one cationic functional group and at least one ultraviolet light-absorbing component is represented by the general formula:

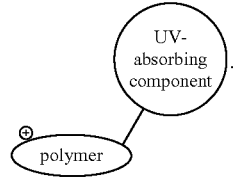

Although the polymer depicted above includes a single positive charge and a single ultraviolet light-absorbing component, polymers with multiple positive charges and/or multiple ultraviolet light-absorbing components are contemplated.

In some aspects, an ultraviolet light-absorbing polymer comprising at least one cationic functional group and at least one ultraviolet light-absorbing molecule covalently bound to the polymer, is provided. In some embodiments, the polymer is a polysiloxane. In some aspects, the ultraviolet light-absorbing polysiloxane polymer is represented by the formula:

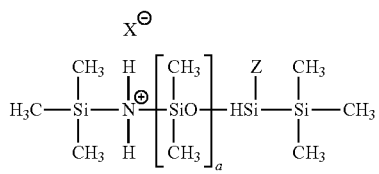

wherein a is an integer ranging from 2 to 100; X is selected from the group consisting of halide, sulfate, phosphate, benzoate, citrate, acetate, mesylate, nitrate, or fumarate; and Z is an ultraviolet light-absorbing moiety. In some embodiments, the ultraviolet light-absorbing moiety is selected from the group consisting of a avobenzone, benzimidazole, benzoxazole, benzotriazole, benzophenone, benzalmalonic acid ester, camphor, cinnamate, dibenzoylmethane, dihydropyrane, homosalate, imidazole, octinoxate, octisalate, octocrylene, oxybenzone, p-aminobenzoate, salicylate, triazone, or a derivative thereof.

In further aspects, the ultraviolet light-absorbing polysiloxane polymer is represented by the formula:

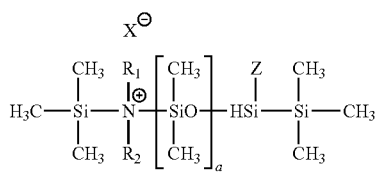

wherein a is an integer ranging from 2 to 100; X is selected from the group consisting of halide, sulfate, phosphate, benzoate, citrate, acetate, mesylate, nitrate, or fumarate; $R_1$ and $R_2$ are independently hydrogen or alkyl; and Z is an ultraviolet light-absorbing moiety. In some embodiments, the ultraviolet light-absorbing moiety is selected from the group consisting of a avobenzone, benzimidazole, benzoxazole, benzotriazole, benzophenone, benzalmalonic acid ester, camphor, cinnamate, dibenzoylmethane, dihydropyrane, homosalate, imidazole, octinoxate, octisalate, octocrylene, oxybenzone, p-aminobenzoate, salicylate, triazone, or a derivative thereof.

In some embodiments, the ultraviolet light-absorbing polysiloxane polymer is represented by the formula:

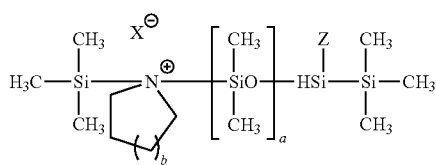

wherein a is an integer ranging from 2 to 100; b is an integer ranging from 0 to 3; X is selected from the group consisting halide, sulfate, phosphate, benzoate, citrate, acetate, mesylate, nitrate, or fumarate; and Z is an ultraviolet light-absorbing moiety. In some embodiments, the ultraviolet light-absorbing moiety is selected from the group consisting of a avobenzone, benzimidazole, benzoxazole, benzotriazole, benzophenone, benzalmalonic acid ester, camphor, cinnamate, dibenzoylmethane, dihydropyrane, homosalate, imidazole, octinoxate, octisalate, octocrylene, oxybenzone, p-aminobenzoate, salicylate, triazone, or a derivative thereof.

In some aspects, the ultraviolet light-absorbing polysiloxane polymer is represented by the formula:

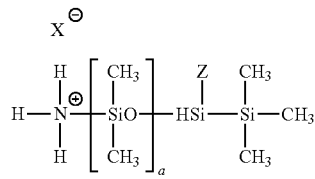

wherein a is an integer ranging from 2 to 100; X is selected from the group consisting of halide, sulfate, phosphate, benzoate, citrate, acetate, mesylate, nitrate, or fumarate; and Z is an ultraviolet light-absorbing moiety. In some embodiments, the ultraviolet light-absorbing moiety is selected from the group consisting of a avobenzone, benzimidazole, benzoxazole, benzotriazole, benzophenone, benzalmalonic acid ester, camphor, cinnamate, dibenzoylmethane, dihydropyrane, homosalate, imidazole, octinoxate, octisalate, octocrylene, oxybenzone, p-aminobenzoate, salicylate, triazone, or a derivative thereof.

In further aspects, the ultraviolet light-absorbing polysiloxane polymer is represented by the formula:

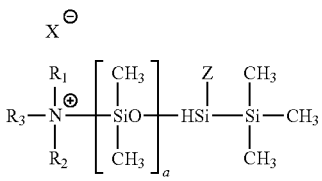

wherein a is an integer ranging from 2 to 100; X is selected from the group consisting of halide, sulfate, phosphate, benzoate, citrate, acetate, mesylate, nitrate, and fumarate; $R_1$, $R_2$, and $R_3$ are independently hydrogen or alkyl; and Z is an ultraviolet light-absorbing moiety. In some aspects, the ultraviolet light-absorbing moiety is selected from the group consisting of a avobenzone, benzimidazole, benzoxazole, benzotriazole, benzophenone, benzalmalonic acid ester, camphor, cinnamate, dibenzoylmethane, dihydropyrane, homosalate, imidazole, octinoxate, octisalate, octocrylene, oxybenzone, p-aminobenzoate, salicylate, triazone, or a derivative thereof.

In additional embodiments, the ultraviolet light-absorbing polysiloxane polymer is represented by the formula:

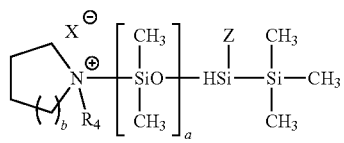

wherein a is an integer ranging from 2 to 100; b is an integer ranging from 0 to 2; X is selected from the group consisting of halide, sulfate, phosphate, benzoate, citrate, acetate, mesylate, nitrate, and fumarate; $R_4$ is hydrogen or alkyl; and Z is an ultraviolet light-absorbing moiety. In some embodiments, the ultraviolet light-absorbing moiety is selected from the group consisting of a avobenzone, benzimidazole, benzoxazole, benzotriazole, benzophenone, benzalmalonic acid ester, camphor, cinnamate, dibenzoylmethane, dihydropyrane, homosalate, imidazole, octinoxate, octisalate, octocrylene, oxybenzone, p-aminobenzoate, salicylate, triazone, or a derivative thereof.

In some embodiments, a sunscreen composition comprising a carrier and an effective amount of an ultraviolet light-absorbing polysiloxane polymer is provided. In further embodiments, a haircare composition comprising a carrier and an effective amount of an ultraviolet light-absorbing polysiloxane polymer is provided. In some embodiments, an ultraviolet light-absorbing polysiloxane polymer improves the rheological stability of a sunscreen or haircare composition.

In further aspects, a method for maintaining an emulsion is provided, the method comprising emulsifying an ultraviolet light-absorbing polysiloxane polymer with an emulsion. The emulsion may be an oil-in-water emulsion or a water-in-oil emulsion. In some embodiments, an ultraviolet light-absorbing polysiloxane polymer improves the rheological stability of an emulsion.

In some aspects, an ultraviolet light-absorbing PEG polymer comprising at least one cationic functional group and at least one ultraviolet light-absorbing molecule covalently bound to the PEG polymer is provided. In other aspects, an ultraviolet light-absorbing PPG polymer comprising at least one cationic functional group and at least one ultraviolet light-absorbing molecule covalently bound to the PPG polymer is provided. In further aspects, an ultraviolet light-absorbing PEG/PPG copolymer comprising at least one cationic functional group and at least one ultraviolet light-absorbing molecule covalently bound to the PEG/PPG copolymer is provided.

In some embodiments, the ultraviolet light-absorbing PEG/PPG copolymer is represented by the formula:

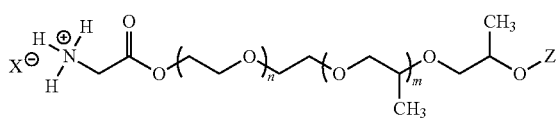

wherein n is an integer ranging from 1 to 100; m is an integer ranging from 1 to 100; X is selected from the group consisting of halide, sulfate, phosphate, benzoate, citrate, acetate, mesylate, nitrate, or fumarate; and Z is an ultraviolet light-absorbing moiety. In some embodiments, the ultraviolet light-absorbing moiety is selected from the group consisting of a avobenzone, benzimidazole, benzoxazole, benzotriazole, benzophenone, benzalmalonic acid ester, camphor, cinnamate, dibenzoylmethane, dihydropyrane, homosalate, imidazole, octinoxate, octisalate, octocrylene, oxybenzone, p-aminobenzoate, salicylate, triazone, or a derivative thereof.

In other aspects, the ultraviolet light-absorbing PEG/PPG copolymer is represented by the formula:

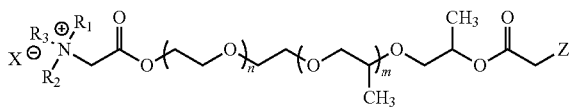

wherein $R_1$, $R_2$, and $R_3$ are each independently hydrogen or alkyl; n is an integer ranging from 1 to 100; m is an integer ranging from 1 to 100; X is selected from the group consisting of halide, sulfate, phosphate, benzoate, citrate, acetate, mesylate, nitrate, or fumarate; and Z is an ultraviolet light-absorbing moiety. In some embodiments, the ultraviolet light-absorbing moiety is selected from the group consisting of a avobenzone, benzimidazole, benzoxazole, benzotriazole, benzophenone, benzalmalonic acid ester, camphor, cinnamate, dibenzoylmethane, dihydropyrane, homosalate, imidazole, octinoxate, octisalate, octocrylene, oxybenzone, p-aminobenzoate, salicylate, triazone, or a derivative thereof.

In further embodiments, the ultraviolet light-absorbing PEG/PPG copolymer is represented by the formula:

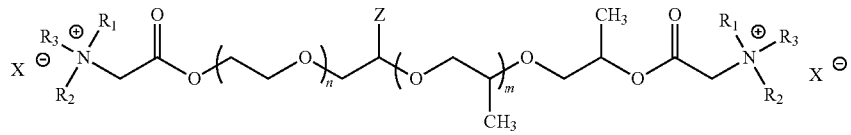

wherein $R_1$, $R_2$, and $R_3$ are each independently hydrogen or alkyl; n is an integer ranging from 1 to 100; m is an integer ranging from 1 to 100; X is selected from the group consisting of halide, sulfate, phosphate, benzoate, citrate, acetate, mesylate, nitrate, or fumarate; and Z is an ultraviolet light-absorbing moiety. In some embodiments, the ultraviolet light-absorbing moiety is selected from the group consisting of a avobenzone, benzimidazole, benzoxazole, benzotriazole, benzophenone, benzalmalonic acid ester, camphor, cinnamate, dibenzoylmethane, dihydropyrane, homosalate, imidazole, octinoxate, octisalate, octocrylene, oxybenzone, p-aminobenzoate, salicylate, triazone, or a derivative thereof.

In some aspects, a method of using a sunscreen or hair color-protecting composition comprises applying to the hair or skin a composition comprising an ultraviolet light-absorbing polymer comprising at least one cationic functional group and at least one ultraviolet light-absorbing molecule covalently bound to the polymer. In some embodiments, the polymer is a polysiloxane, PEG, PPG, or PEG/PPG copolymer. In some aspects, the ultraviolet light-absorbing polymer comprising at least one cationic functional group and at least one ultraviolet light-absorbing component is represented by the general formula:

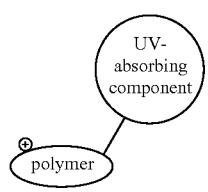

In some aspects, a method of using a sunscreen or hair color-protecting composition comprises applying to the hair or skin a composition comprising a polymer represented by the formula:

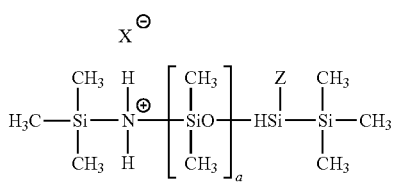

wherein a is an integer ranging from 2 to 100; X is selected from the group consisting of halide, sulfate, phosphate, benzoate, citrate, acetate, mesylate, nitrate, or fumarate; and Z is an ultraviolet light-absorbing moiety. In some embodiments, the ultraviolet light-absorbing moiety is selected from the group consisting of a avobenzone, benzimidazole, benzoxazole, benzotriazole, benzophenone, benzalmalonic acid ester, camphor, cinnamate, dibenzoylmethane, dihydropyrane, homosalate, imidazole, octinoxate, octisalate, octocrylene, oxybenzone, p-aminobenzoate, salicylate, triazone, or a derivative thereof.

In some aspects, a method of using a sunscreen or hair color-protecting composition comprises applying to the hair or skin a composition comprising a polymer represented by the formula:

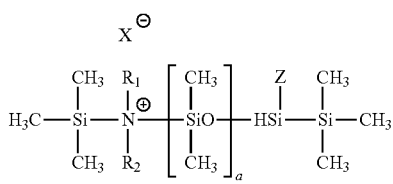

wherein a is an integer ranging from 2 to 100; X is selected from the group consisting of halide, sulfate, phosphate, benzoate, citrate, acetate, mesylate, nitrate, or fumarate; $R_1$ and $R_2$ are independently hydrogen or alkyl; and Z is an ultraviolet light-absorbing moiety. In some embodiments, the ultraviolet light-absorbing moiety is selected from the group consisting of a avobenzone, benzimidazole, benzoxazole, benzotriazole, benzophenone, benzalmalonic acid ester, camphor, cinnamate, dibenzoylmethane, dihydropyrane, homosalate, imidazole, octinoxate, octisalate, octocrylene, oxybenzone, p-aminobenzoate, salicylate, triazone, or a derivative thereof.

In some aspects, a method of using a sunscreen or hair color-protecting composition comprises applying to the hair or skin a composition comprising a polymer represented by the formula:

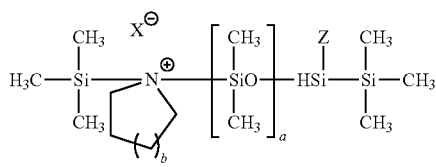

wherein a is an integer ranging from 2 to 100; b is an integer ranging from 0 to 3; X is selected from the group consisting halide, sulfate, phosphate, benzoate, citrate, acetate, mesylate, nitrate, or fumarate; and Z is an ultraviolet light-absorbing moiety. In some embodiments, the ultraviolet light-absorbing moiety is selected from the group consisting of a avobenzone, benzimidazole, benzoxazole, benzotriazole, benzophenone, benzalmalonic acid ester, camphor, cinnamate, dibenzoylmethane, dihydropyrane, homosalate, imidazole, octinoxate, octisalate, octocrylene, oxybenzone, p-aminobenzoate, salicylate, triazone, or a derivative thereof.

In some aspects, a method of using a sunscreen or hair color-protecting composition comprises applying to the hair or skin a composition comprising a polymer represented by the formula:

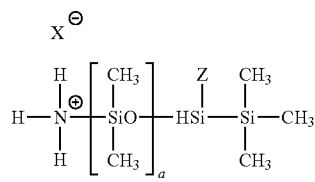

wherein a is an integer ranging from 2 to 100; X is selected from the group consisting of halide, sulfate, phosphate, benzoate, citrate, acetate, mesylate, nitrate, or fumarate; and Z is an ultraviolet light-absorbing moiety. In some embodiments, the ultraviolet light-absorbing moiety is selected from the group consisting of a avobenzone, benzimidazole, benzoxazole, benzotriazole, benzophenone, benzalmalonic acid ester, camphor, cinnamate, dibenzoylmethane, dihydropyrane, homosalate, imidazole, octinoxate, octisalate, octocrylene, oxybenzone, p-aminobenzoate, salicylate, triazone, or a derivative thereof.

In some aspects, a method of using a sunscreen or hair color-protecting composition comprises applying to the hair or skin a composition comprising a polymer represented by the formula:

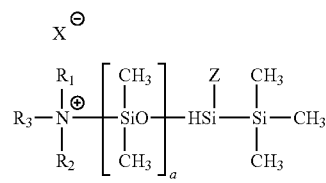

wherein a is an integer ranging from 2 to 100; X is selected from the group consisting of halide, sulfate, phosphate, benzoate, citrate, acetate, mesylate, nitrate, and fumarate; $R_1$, $R_2$, and $R_3$ are independently hydrogen or alkyl; and Z is an ultraviolet light-absorbing moiety. In some aspects, the ultraviolet light-absorbing moiety is selected from the group consisting of a avobenzone, benzimidazole, benzoxazole, benzotriazole, benzophenone, benzalmalonic acid ester, camphor, cinnamate, dibenzoylmethane, dihydropyrane, homosalate, imidazole, octinoxate, octisalate, octocrylene, oxybenzone, p-aminobenzoate, salicylate, triazone, or a derivative thereof.

In some aspects, a method of using a sunscreen or hair color-protecting composition comprises applying to the hair or skin a composition comprising a polymer represented by the formula:

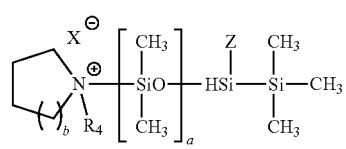

wherein a is an integer ranging from 2 to 100; b is an integer ranging from 0 to 2; X is selected from the group consisting of halide, sulfate, phosphate, benzoate, citrate, acetate, mesylate, nitrate, and fumarate; $R_4$ is hydrogen or alkyl; and Z is an ultraviolet light-absorbing moiety. In some embodiments, the ultraviolet light-absorbing moiety is selected from the group consisting of a avobenzone, benzimidazole, benzoxazole, benzotriazole, benzophenone, benzalmalonic acid ester, camphor, cinnamate, dibenzoylmethane, dihydropyrane, homosalate, imidazole, octinoxate, octisalate, octocrylene, oxybenzone, p-aminobenzoate, salicylate, triazone, or a derivative thereof.

In some aspects, a method of using a sunscreen or hair color-protecting composition comprises applying to the hair or skin a composition comprising a polymer represented by the formula:

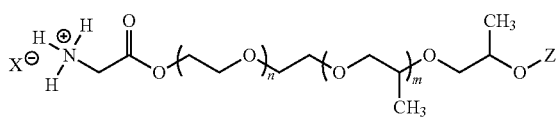

wherein n is an integer ranging from 1 to 100; m is an integer ranging from 1 to 100; X is selected from the group consisting of halide, sulfate, phosphate, benzoate, citrate, acetate, mesylate, nitrate, or fumarate; and Z is an ultraviolet light-absorbing moiety. In some embodiments, the ultraviolet light-absorbing moiety is selected from the group consisting of a avobenzone, benzimidazole, benzoxazole, benzotriazole, benzophenone, benzalmalonic acid ester, camphor, cinnamate, dibenzoylmethane, dihydropyrane, homosalate, imidazole, octinoxate, octisalate, octocrylene, oxybenzone, p-aminobenzoate, salicylate, triazone, or a derivative thereof.

In some aspects, a method of using a sunscreen or hair color-protecting composition comprises applying to the hair or skin a composition comprising a polymer represented by the formula:

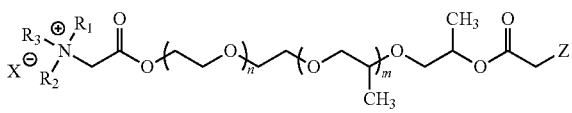

wherein $R_1$, $R_2$, and $R_3$ are each independently hydrogen or alkyl; n is an integer ranging from 1 to 100; m is an integer ranging from 1 to 100; X is selected from the group consisting of halide, sulfate, phosphate, benzoate, citrate, acetate, mesylate, nitrate, or fumarate; and Z is an ultraviolet light-absorbing moiety. In some embodiments, the ultraviolet light-absorbing moiety is selected from the group consisting of a avobenzone, benzimidazole, benzoxazole, benzotriazole, benzophenone, benzalmalonic acid ester, camphor, cinnamate, dibenzoylmethane, dihydropyrane, homosalate, imidazole, octinoxate, octisalate, octocrylene, oxybenzone, p-aminobenzoate, salicylate, triazone, or a derivative thereof.

In some aspects, a method of using a sunscreen or hair color-protecting composition comprises applying to the hair or skin a composition comprising a polymer represented by the formula:

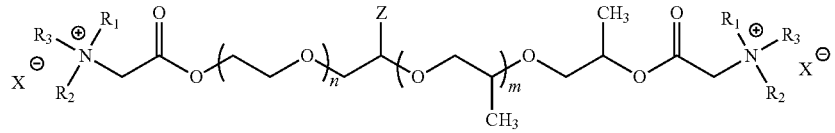

wherein $R_1$, $R_2$, and $R_3$ are each independently hydrogen or alkyl; n is an integer ranging from 1 to 100; m is an integer ranging from 1 to 100; X is selected from the group consisting of halide, sulfate, phosphate, benzoate, citrate, acetate, mesylate, nitrate, or fumarate; and Z is an ultraviolet light-absorbing moiety. In some embodiments, the ultraviolet light-absorbing moiety is selected from the group consisting of a avobenzone, benzimidazole, benzoxazole, benzotriazole, benzophenone, benzalmalonic acid ester, camphor, cinnamate, dibenzoylmethane, dihydropyrane, homosalate, imidazole, octinoxate, octisalate, octocrylene, oxybenzone, p-aminobenzoate, salicylate, triazone, or a derivative thereof.

In some aspects, a method of using a sunscreen or hair color-protecting composition comprises applying to the hair or skin a composition comprising a polymer as disclosed herein.

In some embodiments, a sunscreen composition comprising a carrier and an effective amount of an ultraviolet light-absorbing PEG polymer is provided. In further embodiments, a sunscreen composition comprising a carrier and an effective amount of an ultraviolet light-absorbing PPG polymer is provided. In additional embodiments, a sunscreen composition comprising a carrier and an effective amount of an ultraviolet light-absorbing PEG/PPG copolymer is provided.

In some aspects, a haircare composition comprising a carrier and an effective amount of an ultraviolet light-absorbing PEG polymer is provided. In additional aspects, a haircare composition comprising a carrier and an effective amount of an ultraviolet light-absorbing PPG polymer is provided. In further embodiments, a haircare composition comprising a carrier and an effective amount of an ultraviolet light-absorbing PEG/PPG copolymer is provided. In some embodiments, an ultraviolet light-absorbing PEG polymer, PPG polymer, or PEG/PPG copolymer improves the rheological stability of a sunscreen composition. In further embodiments, an ultraviolet light-absorbing PEG polymer, PPG polymer, or PEG/PPG copolymer improves the rheological stability of a sunscreen composition.

In some embodiments, a method for maintaining an emulsion is provided, the method comprising emulsifying an ultraviolet light-absorbing PEG polymer, PPG polymer, or PEG/PPG copolymer with an emulsion. The emulsion may be an oil-in-water emulsion or a water-in-oil emulsion. In further embodiments, an ultraviolet light-absorbing PEG polymer, PPG polymer, or PEG/PPG copolymer improves the rheological stability of an emulsion.

The terms "a" and "an" are defined as one or more unless this disclosure explicitly requires otherwise. The term "substantially" is defined as being largely but not necessarily wholly what is specified (and include wholly what is specified) as understood by one of ordinary skill in the art. In any disclosed embodiment, the term "substantially" may be substituted with "within [a percentage] of" what is specified, where the percentage includes 0.1, 1, 5, and 10 percent. The terms "moiety", "functional group", "component", and "compound" may be used interchangeably herein.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an ultraviolet light-absorbing polymer that "comprises," "has," "includes" or "contains" one or more elements possesses those one or more elements, but is not limited to possessing only those one or more elements. Likewise, an element of a system or composition that "comprises," "has," "includes" or "contains" one or more features possesses those one or more features, but is not limited to possessing only those one or more features.

Furthermore, a structure or composition that is configured in a certain way is configured in at least that way, but may also be configured in ways that are not listed. Metric units may be derived from the English units provided by applying a conversion and rounding to the nearest millimeter.

The feature or features of one embodiment may be applied to other embodiments, even though not described or illustrated, unless expressly prohibited by this disclosure or the nature of the embodiments. In any of the claims, the term "consisting of" or "consisting essentially of" can be substituted for any of the open-ended linking verbs recited above, in order to change the scope of a given claim from what it would otherwise be using the open-ended linking verb.

Kits that include the compositions of the present invention are also contemplated. In certain embodiments, the composition is comprised in a container. The container can be a bottle, dispenser, or package. The container can dispense a pre-determined amount of the composition. In certain aspects, the compositions is dispensed in a spray, mist, dollop, or liquid. The container can include indicia on its surface. The indicia can be a word, an abbreviation, a picture, or a symbol.

It is also contemplated that the compositions disclosed throughout this specification can be used as a leave-on or rinse-off composition. By way of example, a leave-on composition can be one that is topically applied to skin or hair and remains on the skin or hair for a period of time (e.g., at least 5, 6, 7, 8, 9, 10, 20, or 30 minutes, or at least 1, 2, 3, 4, 5, 6, 7, 8, 9, 10, 11, 12, 13, 14, 15, 16, 17, 18, 19, 20, 21, 22, 23 or 24 hours, or overnight or throughout the day). Alternatively, a rinse-off composition can be a product that is intended to be applied to the skin or hair and then removed or rinsed from the skin or hair (e.g., with water) within a period of time such as less than 5, 4, 3, 2, or 1 minute. An example of a rinse off composition can be a skin cleanser, shampoo, conditioner, or soap. An example of a leave-on composition can be a skin moisturizer, sunscreen, mask, overnight cream, or a day cream.

It is contemplated that any embodiment discussed in this specification can be implemented with respect to any method or composition of the invention, and vice versa. Furthermore, compositions of the invention can be used to achieve methods of the invention.

In one embodiment, compositions of the present invention can be pharmaceutically or cosmetically elegant or can have pleasant tactile properties. "Pharmaceutically elegant," "cosmetically elegant," and/or "pleasant tactile properties" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a gel, a wash, a foundation, a night cream, a lipstick, a cleanser, a toner, a sunscreen, a hair color-protecting composition, a mask, an anti-aging product, a deodorant, an antiperspirant, a perfume, a cologne, a shampoo, a conditioner, etc.

A hair color-protecting composition as used herein may refer to a product that can be used to clean, treat or style hair. Examples of hair color-protecting compositions include, but are not limited to shampoos, conditioners, styling gels, aerosol styling sprays, non-aerosol styling sprays, aerosol styling mousses, styling gels, styling pomades, leave-in conditioning sprays, and thermal protection sprays.

"Topical application" means to apply or spread a composition onto the surface of lips or keratinous tissue. "Topical skin composition" includes compositions suitable for topical application on skin and/or keratinous tissue. Such compositions are typically dermatologically-acceptable in that they do not have undue toxicity, incompatibility, instability, allergic response, and the like, when applied to skin and/or keratinous tissue. Topical skin care compositions of the present invention can have a selected viscosity to avoid significant dripping or pooling after application to skin and/or keratinous tissue.

"Keratinous tissue" includes keratin-containing layers disposed as the outermost protective covering of mammals and includes, but is not limited to, lips, skin, hair, and nails.

The term "about" or "approximately" are defined as being close to as understood by one of ordinary skill in the art. In one non-limiting embodiment the terms are defined to be within 10%, preferably within 5%, more preferably within 1%, and most preferably within 0.5%.

The term "substantially" and its variations are refers to ranges within 10%, within 5%, within 1%, or within 0.5%.

The terms "inhibiting" or "reducing" or any variation of these terms includes any measurable decrease or complete inhibition to achieve a desired result. The terms "promote" or "increase" or any variation of these terms includes any measurable increase or production of a protein or molecule (e.g., matrix proteins such as fibronectin, laminin, collagen, or elastin or molecules such as hyaluronic acid) to achieve a desired result.

The term "effective," as that term is used in the specification and/or claims, means adequate to accomplish a desired, expected, or intended result.

The use of the word "a" or "an" when used in conjunction with the terms "comprising," "including," "having," or "containing," or any variations of these terms, in the claims and/or the specification may mean "one," but it is also consistent with the meaning of "one or more," "at least one," and "one or more than one."

The compositions and methods for their use can "comprise," "consist essentially of," or "consist of" any of the ingredients or steps disclosed throughout the specification.

With respect to the phrase "consisting essentially of," a basic and novel property of the compositions and methods of the present invention is the ability to reduce skin erythema and reduce skin temperature.

Other objects, features, and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DETAILED DESCRIPTION

As noted above, the unique aspects of the present invention are ultraviolet light-absorbing molecules with improved rheological properties. The union of a polymer with an ultraviolet light-absorbing agent allows the ultraviolet light-absorbing component to remain in solutions, emulsions, dispersions, etc. longer than its non-polymeric counterpart. The inclusion of one or more positive charges provides a means for interacting with cling to and skin and hair tissue. Disclosed herein are polymers bearing at least one ultraviolet light-absorbing group and at least one cationic moiety. The ultraviolet light-absorbing polymers may be used in and for the preparation of cosmetic or dermatological composition, including sunscreens and hair color-protecting compositions. The compositions therefore protect the skin and/or hair against the harmful effects of UV radiation, in particular solar radiation. Polymers that are chemically bound to a ultraviolet light-absorbing component will help the ultraviolet light-absorbing component stay in the oil phase. The inclusion of a cationic functional group on a polymer bound to an ultraviolet light-absorbing component may increase the hydrophilicity of the polymer and assist in maintaining emulsions and/or suspensions. A successful emulsion or suspension will improve SPF per unit sunscreen, which allow less ultraviolet light-absorbing compound to be used. Benefits associated with cationic polymers that are bound to at least one ultraviolet light-absorbing compound include shielding skin and/or hair from ultraviolet light. A cationic polymer bound to at least one ultraviolet light-absorbing compound may protect natural or color-treated hair by slowing down the oxidation process, color-fastness, integrity, conditioning, and color softness.

A. Ultraviolet Light-Absorbing Groups

Ultraviolet light-absorbing groups comprise chemical functional groups or moieties which absorb light in the range of wavelengths 400-320 nm (UVA), 320-200 nm (UVB), and/or 100-280 nm (UVC). Ultraviolet light-absorbing groups disclosed herein include but are not limited to avobenzone (e.g., 1-(4-methoxyphenyl)-3-(4-t-butylphenyl) propane-1,3-dione), benzimidazole (e.g., 2-phenylbenzimidazole-5-sulfonic acid), benzoxazole (e.g., 5-tert-butyl-1,3 benzoxazole), benzotriazole (e.g., 2-(2-hydroxy-5-methyl-phenyl)-benzotriazole), benzophenone (e.g., diethylamino dihydroxybenzoyl hexyl benzoate), benzalmalonic acid ester (e.g., di-(2-ethylhexyl) 4-methoxybenzalmalonate), camphor (e.g., 4-methyl benzylidene camphor), cinnamate (e.g., octyl methoxycinnamate), dibenzoylmethane (e.g., 4-t-butyl-4'-methoxy dibenzoyl-methane), dihydropyran (3,4-dihydropyran-2-carboxylate), homosalate (e.g., 3,3,5-trimethylcyclohexyl 2-hydroxybenzoate), imidazole (e.g., 2-phenyl benzimidazole sulfonic acid and its salts), octocrylene (2-ethylhexyl 2-cyano-3,3-diphenyl-2-propenoate), oxybenzone, p-aminobenzoate (e.g., 4-amino benzoic acid-2,3-dihydroxypropyl ester), salicylate (e.g., octyl salicylate), triazone (e.g., octyl triazone), or a derivative thereof. One or more additional ultraviolet light-absorbing compounds may be added to the sunscreen or haircare compositions. The combination of multiple ultraviolet light-absorbing compounds and moieties may have additive or synergistic effects.

B. Additives

The sunscreen and hair color-protecting compositions may include one or more of each of an ultraviolet light-absorbing polymer, a non-ionic, anionic, cationic, or zwitterionic surfactant, vitamins, pH adjusters, fragrance, solvents, preservatives, emulsifying agents, softeners, fillers, moisturizers, dyes, colorants, pigments, antifoaming agents, antioxidants, moisturizing agents, essential oils, thickening agents, pharmaceutically-active agents, and other additives used by those skilled in the art.

C. Surfactants

Exemplary surfactants include but are not limited to cocamidopropyl betaine, coco betaine, lauryl betaine, oleyl betaine, stearyl betaine, coco sultaine, lauryl sultaine, sodium cocoyl isethionate, sodium methyl 2-sulfolaurate, disodium 2-sulfolaurate, sodium lauryl sulfoacetate, ammonium lauryl sulfate, ammonium laureth sulfate, sodium lauryl sulfate, sodium laureth sulfate, sodium lauroyl sarcosinate, cocoyl sarcosine, sodium cocoyl lactylate, sodium cocoyl sarcosinate.

D. Vitamins

Non-limiting examples of vitamins that may be added to the present compositions include niacinamide, sodium starch octenylsuccinate, calcium pantothenate, maltodextrin, sodium ascorbyl phosphate, pyridoxine HCl, silica, panthenol, phytantriol, calcium pantothenate, vitamin E, and vitamin E esters (e. g., tocopheryl acetate, tocopheryl nocotinate, tocopheryl palmitate, or tocopheryl retinoate).

E. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, *macadamia* nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, *eucalyptus* oil, fennel oil, sea fennel oil, frankincense oil, *geranium* oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

F. pH Adjusters

Non-limiting examples of pH adjusters that may be used with the present compositions include common acids and bases, including but not limited to citric acid, acetic acid, benzoic acid, glycolic acid, lactic acid, malic acid, potassium hydroxide, potassium carbonate, sodium carbonate, sodium hydroxide, ethanolamine, and triethanolamine.

G. Solvents

Non-limiting examples of solvents that may be included in the present ultraviolet light-absorbing compositions include but are not limited to water, propylene glycol, propane diol, glycerol, SD alcohol, mineral oil, butanediol, cyclomethicone, and ethoxyglycol.

H. Preservatives

Non-limiting examples of preservatives that may be included in the present ultraviolet light-absorbing compositions include but are not limited to benzoic acid, benzoic acid salts, benzyl alcohol, butylparaben, propylparaben, methyparaben, methylisothiazolinone, methylchloroisothiazolinone, phenoxy-ethanol, quaterium-8, quaterium-14, quaterium-15, triclosan, zinc pyrithione, zinc salicylate, quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

I. Emulsifying Agents

Non-limiting examples of emulsifying agents that can be used with the present compositions include nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, cetearyl glucoside, cetearyl alcohol, C12-13 pareth-3, PPG-2 methyl glucose ether di stearate, PPG-5-ceteth-20, bis-PEG/PPG-20/20 dimethicone, ceteth-10, polysorbate 80, cetyl phosphate, potassium cetyl phosphate, diethanolamine cetyl phosphate, polysorbate 60, glyceryl stearate, PEG-100 stearate, arachidyl alcohol, arachidyl glucoside, and mixtures thereof.

J. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

K. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrrolidone carboxylic acid, potassium PCA, propylene glycol, saccharide isomerate, sodium glucuronate, sodium PCA, sorbitol, sucrose, trehalose, urea, and xylitol.

Other examples include acetylated lanolin, acetylated lanolin alcohol, alanine, algae extract, *Aloe barbadensis*, *Aloe barbadensis* extract, *Aloe barbadensis* gel, *Althea officinalis* extract, apricot (*Prunus armeniaca*) kernel oil, arginine, arginine aspartate, *Arnica montana* extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamom (*Elettaria cardamomum*) oil, carnauba (*Copernicia cerifera*) wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *Eucalyptus globulus* oil, evening primrose (*Oenothera biennis*) oil, fatty acids, *Geranium maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, *Macadamia ternifolia* nut oil, maltitol, matricaria (*Chamomilla recutita*) oil, methyl glucose sesquistearate, methylsilanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*Mentha piperita*) oil, petrolatum, phospholipids, plankton extract, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil.

L. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene, trihydroxystearin, ammonium acryloyldimethyltaurate/vp copolymer, or a mixture of them.

Non-limiting examples of additional thickening agents that can be used in the present compositions include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a C10-C30 straight chain or branched chain alkyl group through an ether linkage. Typically these polymers are ethers of C10-C30 straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

M. Pharmaceutically-Active Agents

Pharmaceutically-active agents are also contemplated as being useful with the present compositions. Non-limiting examples of pharmaceutical active agents include anti-acne agents, agents used to treat rosacea, analgesics, anti-inflammatory agents including non-steroidal anti-inflammatory drugs, antibiotics, antifungals, antivirals, antimicrobials, antipsoriatic agents, antiseborrheic agents, biologically active proteins and peptides, burn treatment agents, depigmenting agents, hair growth stimulants, hair growth retardants including DFMO and its salts and analogs, kerotolytics, skin protectant/barrier agents, steroids including hormones and corticosteroids, sunburn treatment agents, etc.

N. Amounts of Ingredients

It is contemplated that the compositions of the present invention can include any amount of the ingredients discussed in this specification. The compositions can also include any number of combinations of additional ingredients described throughout this specification (e.g., pigments, or additional cosmetic or pharmaceutical ingredients). The concentrations of the any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

O. Carriers

The compositions of the present invention can include or be incorporated into all types of carriers and vehicles. The carrier or vehicle can be a pharmaceutically or dermatologically acceptable carrier or vehicle. Non-limiting examples of carriers or vehicles include water, glycerin, alcohol, oil, a silicon containing compound, a silicone compound, and wax. Variations and other appropriate vehicles will be apparent to the skilled artisan and are appropriate for use in the present invention. In certain aspects, the concentrations and combinations of the compounds, ingredients, and agents can be selected in such a way that the combinations are chemically compatible and do not form complexes which precipitate from the finished product.

P. Formulations

The compositions of the present invention can be structured or formulated into a variety of different forms. Non-limiting examples include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, masks, peels, and ointments. Variations and other structures will be apparent to the skilled artisan and are appropriate for use in the present invention.

The invention claimed is:

1. A method of using a sunscreen or hair color-protecting composition comprising applying to the hair or skin a composition comprising an ultraviolet light-absorbing polymer represented by the formula:

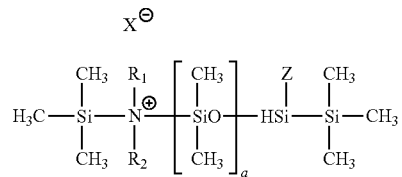

wherein;
a is an integer ranging from 2 to 100;
$R_1$, and $R_2$ are independently hydrogen or alky;
X is selected from the group consisting of halide, sulfate, phosphate, benzoate, citrate, acetate, mesylate, nitrate, and fumarate; and
Z is an ultraviolet light-absorbing moiety selected from the group consisting of an avobenzone, benzimidazole, benzoxazole, benzotriazole, benzophenone, benzalmalonic acid ester, camphor, cinnamate, dibenzoylmethane, dihydropyrane, homosalate, imidazole, octinoxate, octisalate, octocrylene, oxybenzone, p-aminobenzoate, salicylate, triazone, or a derivative thereof.

2. A method of using a sunscreen or hair color-protecting composition comprising applying to the hair or skin a composition comprising an ultraviolet light-absorbing polymer represented by the formula:

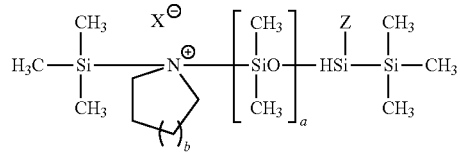

wherein;
a is an integer ranging from 2 to 100;
b is an integer ranging from 0 to 3;

X is selected from the group consisting of halide, sulfate, phosphate, benzoate, citrate, acetate, mesylate, nitrate, and fumarate; and Z is an ultraviolet light-absorbing moiety selected from the group consisting of an avobenzone, benzimidazole, benzoxazole, benzotriazole, benzophenone, benzalmalonic acid ester, camphor, cinnamate, dibenzoylmethane, dihydropyrane, homosalate, imidazole, octinoxate, octisalate, octocrylene, oxybenzone, p-aminobenzoate, salicylate, triazone, or a derivative thereof.

3. A method of using a sunscreen or hair color-protecting composition comprising applying to the hair or skin a composition comprising an ultraviolet light-absorbing polymer represented by the formula:

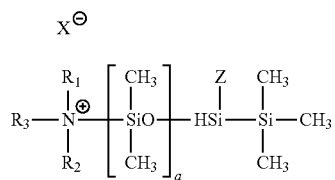

wherein;
a is an integer ranging from 2 to 100;
$R_1$, $R_2$, and $R_3$ are independently hydrogen or alky;
X is selected from the group consisting of halide, sulfate, phosphate, benzoate, citrate, acetate, mesylate, nitrate, and fumarate; and
Z is an ultraviolet light-absorbing moiety selected from the group consisting of an avobenzone, benzimidazole, benzoxazole, benzotriazole, benzophenone, benzalmalonic acid ester, camphor, cinnamate, dibenzoylmethane, dihydropyrane, homosalate, imidazole, octinoxate, octisalate, octocrylene, oxybenzone, p-aminobenzoate, salicylate, triazone, or a derivative thereof.

4. A method of using a sunscreen or hair color-protecting composition comprising applying to the hair or skin a composition comprising an ultraviolet light-absorbing polymer represented by the formula:

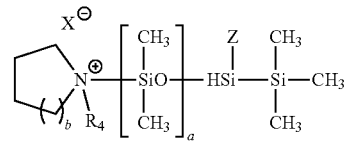

wherein;
a is an integer ranging from 2 to 100;
b is an integer ranging from 0 to 3;
$R_4$ is hydrogen or alky;
X is selected from the group consisting of halide, sulfate, phosphate, benzoate, citrate, acetate, mesylate, nitrate, and fumarate; and
Z is an ultraviolet light-absorbing moiety selected from the group consisting of an avobenzone, benzimidazole, benzoxazole, benzotriazole, benzophenone, benzalmalonic acid ester, camphor, cinnamate, dibenzoylmethane, dihydropyrane, homosalate, imidazole, octinoxate, octisalate, octocrylene, oxybenzone, p-aminobenzoate, salicylate, triazone, or a derivative thereof.

* * * * *